(12) United States Patent
Kawabata et al.

(10) Patent No.: US 7,824,336 B2
(45) Date of Patent: Nov. 2, 2010

(54) ULTRASONIC APPARATUS FOR DIAGNOSIS AND THERAPY

(75) Inventors: Kenichi Kawabata, Kodaira (JP); Nami Sugita, Ranzan (JP); Shinichiro Umemura, Muko (JP)

(73) Assignee: Hitachi, Ltd., Tokyo (JP)

( * ) Notice: Subject to any disclaimer, the term of this patent is extended or adjusted under 35 U.S.C. 154(b) by 206 days.

(21) Appl. No.: 11/336,849

(22) Filed: Jan. 23, 2006

(65) Prior Publication Data

US 2007/0016042 A1 Jan. 18, 2007

(30) Foreign Application Priority Data

May 17, 2005 (JP) ............................. 2005-144367

(51) Int. Cl.
*A61B 8/00* (2006.01)
(52) U.S. Cl. ...................... 600/439; 600/437; 601/2
(58) Field of Classification Search ................ 601/2; 600/437, 439
See application file for complete search history.

(56) References Cited

U.S. PATENT DOCUMENTS

| | | | | |
|---|---|---|---|---|
| 5,215,680 | A | * | 6/1993 | D'Arrigo ................... 516/11 |
| 5,694,936 | A | * | 12/1997 | Fujimoto et al. ........... 600/439 |
| 7,258,674 | B2 | * | 8/2007 | Cribbs et al. .................. 601/2 |
| 2004/0039312 | A1 | | 2/2004 | Hillstead et al. |
| 2004/0131547 | A1 | * | 7/2004 | Balinov et al. ............ 424/9.51 |
| 2004/0158152 | A1 | | 8/2004 | Lizzi |
| 2005/0038340 | A1 | | 2/2005 | Vaezy |

FOREIGN PATENT DOCUMENTS

| WO | WO 94/06380 | 3/1994 |
|---|---|---|
| WO | WO 98/01131 | 1/1998 |

OTHER PUBLICATIONS

Quantitative Analysis and Applications of Non-Invasive Temperature Estimation Using Diagnostic Ultrasound, Simon et al (XP-000800017, Oct. 5, 1997, vol. 2 pp. 1319-1322.
Cancer 2 Nature Rev.2 by T. Allen (2002) pp. 750-763.
Ultrasound in Med. & Biol., vol. 27, No. 10, Holt et al. pp. 1399-1412, (2001).
J. Acoust. Soc. Am. 88 by Holland et al. pp. 2059-2069 (1990).
Ultrasound Contrast Image 92 (Proc. 4th Inter Symp. Kawabata et al. (2004).
Trans IEEE Medical Imag. 23 Alizards et al. pp. 1087-1093 Alizards et al. (2004).
Chinese Office Action issued in corresponding Chinese Patent Application No. 2006100015765.

* cited by examiner

*Primary Examiner*—Brian Casler
*Assistant Examiner*—James Kish
(74) *Attorney, Agent, or Firm*—Antonelli, Terry, Stout & Kraus, LLP.

(57) ABSTRACT

An ultrasonic apparatus for diagnosis and therapy is provided with plural ultrasound probes for generating ultrasound waves for phase shift, diagnosis, and therapy. A first control part causes phase shift in a nano droplet ultrasound contrast agent, while a second control part detects the phase shift of the nano droplet ultrasound contrast agent using ultrasound echo detected by an echo detection device. A difference calculation device calculates a difference of the detected phase shift over time, and a positioning device determines a target position where the difference is produced. A third control part is also provided for exposing a decided target area to the ultrasound waves for therapy.

5 Claims, 6 Drawing Sheets

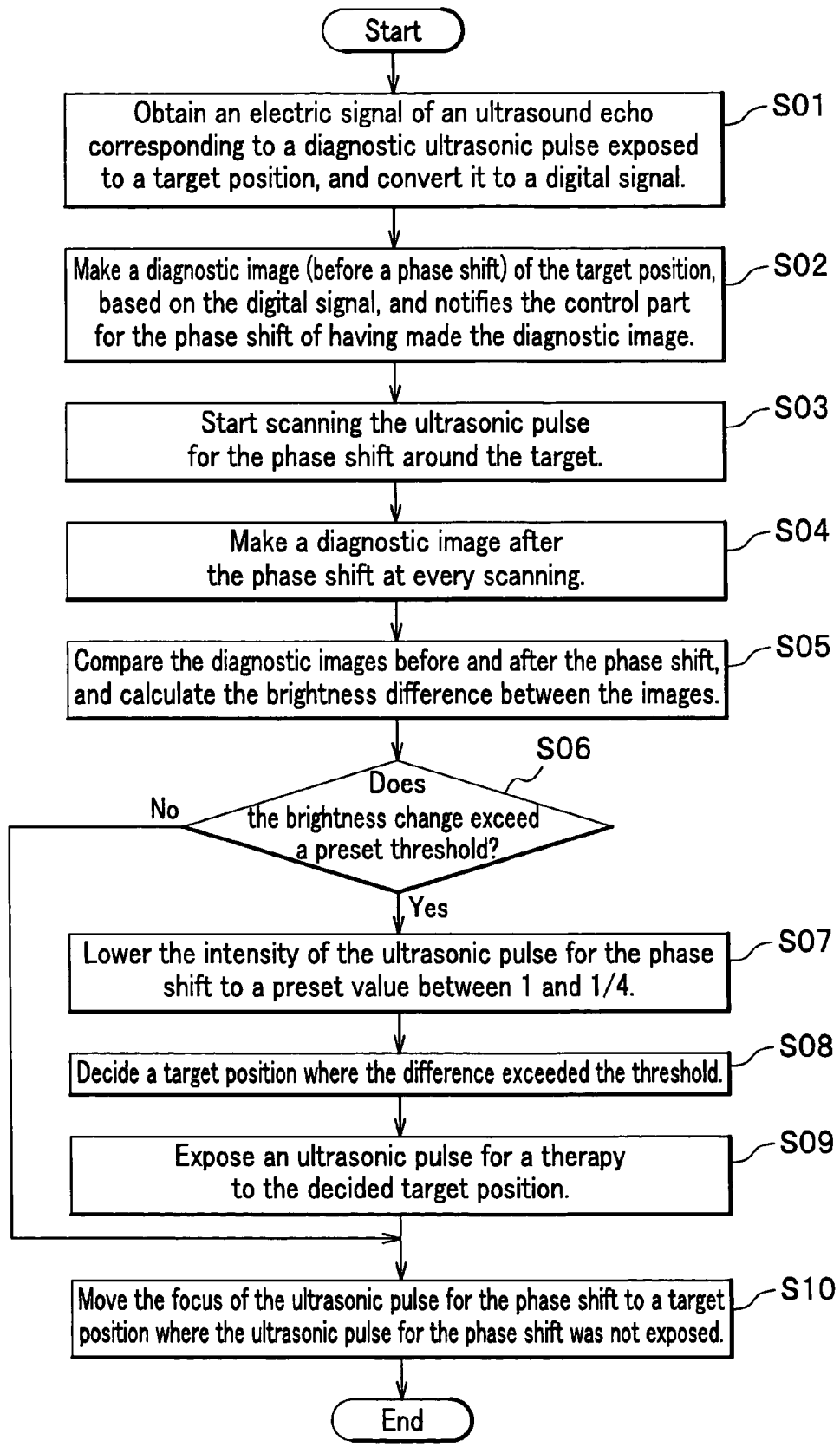

FIG.4A
First Wave
$4W/cm^2$
Second Wave
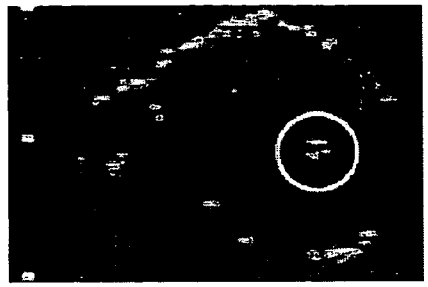
$4W/cm^2$
FIG.4B
$4W/cm^2$
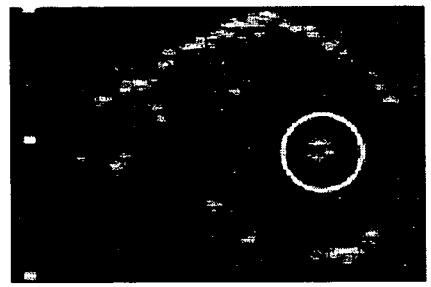
$2W/cm^2$
FIG.4C
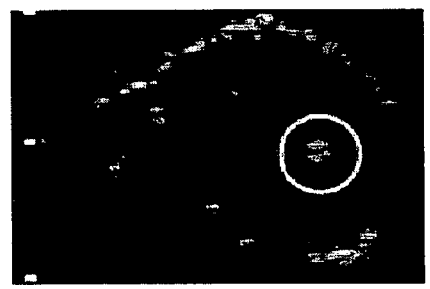
$4W/cm^2$
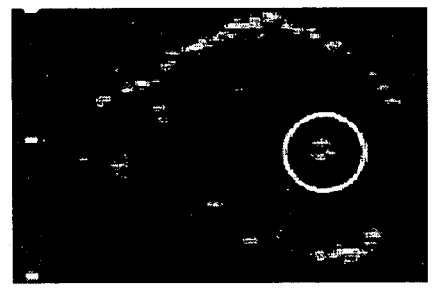
$1W/cm^2$
FIG.4D
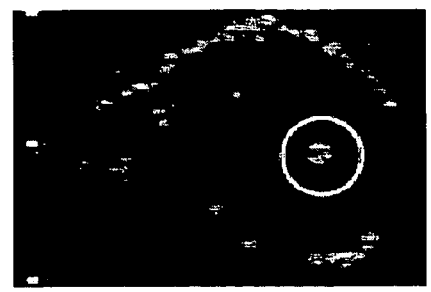
$4W/cm^2$
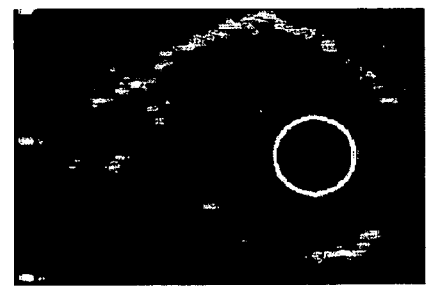
$0.5W/cm^2$

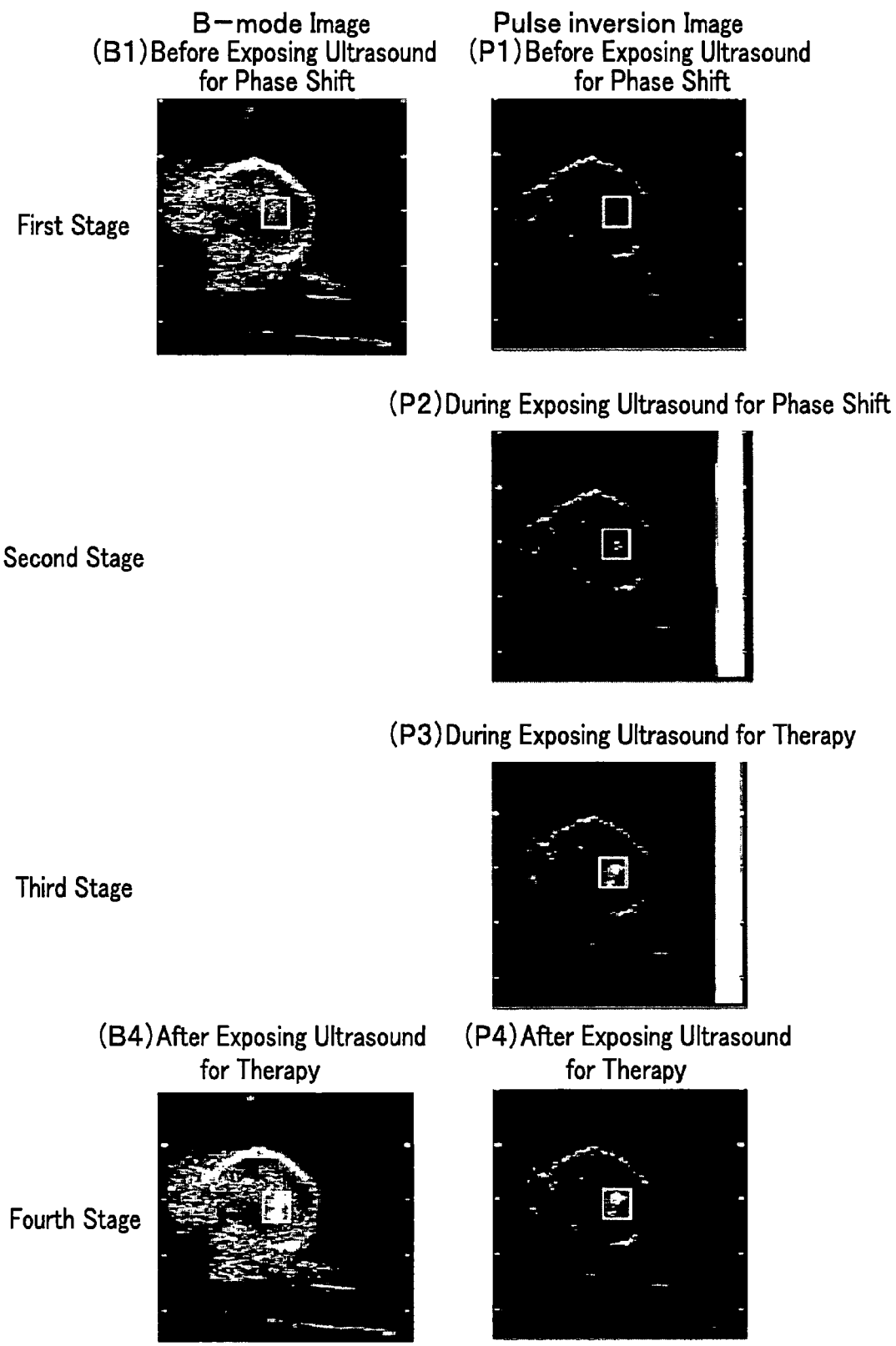

ULTRASONIC APPARATUS FOR DIAGNOSIS AND THERAPY

CROSS REFERENCE TO RELATED APPLICATIONS

The present application claims priority from Japanese application 2005-144367, filed on May 17, 2005, the content of which is hereby incorporated by reference into this application.

BACKGROUND OF THE INVENTION

1. Field of the Invention

The present invention relates to an apparatus for a diagnosis and therapy utilizing an ultrasound, and particularly, to the apparatus for the diagnosis and therapy utilizing the ultrasound used in combination with a phase-shift type ultrasound contrast agent.

2. Description of the Related Art

It is a long time since image diagnostic modalities such as an X-ray CT (Computed Tomography) apparatus, an MRI (Magnetic Resonance Imaging) apparatus, and an apparatus for a diagnosis and therapy became an indispensable tool in clinical settings. These are something where differences of a CT value, a spin relaxation time, and an acoustic impedance within a living body are imaged, respectively, and are called "anatomical imaging" because the differences of these physical properties mainly reflect a living orgasm. On the other hand, something for imaging a target position of a functionally different state is called "functional imaging" even if it is a structurally same tissue.

Out of the functional imaging, for example, something for visualizing an existing state of a living body constitutional molecule such as a protein, an amino acid, and a nucleic acid is called "molecular imaging" in may cases. The molecular imaging is one of research areas that currently get most attention because an application to an elucidation of a life process such as a generation and differentiation and to a diagnosis and therapy of a disease is expected.

As image diagnostic modalities specialized in such the molecular imaging can be cited a PET (Positron Emission Tomography) apparatus and an optical imaging apparatus. The former is broadly used as a tool for classifying a clinical widening extent and proceeding stage of a tumor; the latter as a noninvasive analysis tool of a drug in such a drug development where a small animal is used.

In addition, also in modalities such as the MRI and the ultrasonic apparatus for the diagnosis and therapy where an application as the morph imaging is precedent, a research and development for utilizing them as the molecular imaging progresses.

Furthermore, the ultrasonic apparatus for the diagnosis and therapy is expected as a diagnosis and therapy integration tool usable other than in a big hospital because it has features, which other modalities do not have, such as being 1) excellent in real time property, 2) less in restriction with respect to a use within an operation room thanks to its smallness, and 3) also usable as a therapeutic tool as well as a diagnostic tool.

Here, a therapeutic method of using an ultrasound can be mainly classified into two. One is a thermal coagulation therapy that converges and exposes the ultrasound, heats up a target position not less than a protein denaturation temperature (about 65 degrees Celsius) in a short time of a few seconds, and thereby, treats the target position. Because the thermal coagulation therapy is a therapy of using a high intensity focused ultrasound (HIFU) not less than 1 kW/cm$^2$, it is called an "HIFU" therapy in many cases.

However, if because the HIFU therapy obtains an exposure positional selectivity only due to a convergence of an ultrasound, an aim is missed due to a body movement, there is a possibility that a high intensity ultrasound not less than 1 kW/cm$^2$ is exposed on a target position other than a target position. Therefore, it is preferable that a therapeutic method has the positional selectivity other than the convergence of the ultrasound.

Another therapeutic method for using an ultrasound is a therapy by (acoustic) cavitation action. A cavitation is basically a phenomenon that a bubble nucleus is produced by ultrasound, the bubble grows, and is collapsed. Because if the cavitation occurs, a high temperature of several thousand degrees and a high pressure of several hundreds occur at the collapse stage of a last bubble, it is enabled to treat a target position, utilizing this. Furthermore, it is enabled to more effectively treat the target position by a chemical substance called an acoustic chemical active substance activated by cavitation (for example, see a pamphlet of WO 98/01131).

In any one of the therapeutic methods for using an ultrasound, it is preferable to reduce an ultrasound exposure amount in order to alleviate a burden of an inspected body. Consequently, in order to restrict an exposure range, a method of properly identifying a tumor position is requested.

In general chemical and radio active therapy fields are disclosed methods of utilizing a "molecular probe" for selectively bonding a living body constitutional molecule such as an antibody and a ligand, detecting a tumor, and making the tumor a therapy target (for example, see pages 750-763 in Cancer 2 (Nature Rev. 2) by Allen (2002)). These tumor identification methods are also utilized for an ultrasonic contrast agent used for an ultrasonic apparatus for a diagnosis and therapy.

In addition, if there exist a micro bubble used as an ultrasonic contrast agent, it is well known in exposing an ultrasound that an apparent absorption coefficient becomes higher (for example, see pages 1399-1412, Ultrasound Med. Biol 27 by Holt et al. (2001)). Because if it is possible to restrict the micro bubble only to a target position, it is enabled to selectively heat up the target position with using the phenomenon, it is enabled to reduce an ultrasound exposure amount in a thermal coagulation therapy.

In addition, an existence of a micro bubble in an ultrasound exposure position corresponds to a stage that the bubble on the way of a cavitation process has grown, and it is possible to omit one step of a nucleus production requested for a production of a cavitation by exposing an ultrasound at the stage. Therefore, it is well known that an acoustic intensity requested for the production of the cavitation is reduced by the existence of the micro bubble (for example, see pages 2059-2069 in J. Acoust. Soc. Am. 88 by Holland et al. (1990)). In other words, if it is possible to restrict a micro bubble to a target position, with using the phenomenon it is enabled to reduce an ultrasound exposure amount in a therapy by cavitation action.

However, because a micro bubble cannot exist only in a blood vessel due to a restriction of a size thereof, it is difficult to restrict the bubble to a specific position of a tissue.

Consequently, a phase-shift type ultrasound contrast agent is disclosed that is a droplet of a nano size when dosed in a living body, produces a phase shift by ultrasound exposure, and thereby produces a micro bubble (for example, see Ultrasound Contrast Image 92 (Proc. 4$^{th}$ Intern Symp.) by Kawabata et al. (2004)). It is possible to move the droplet of the nano size if any to a tissue such as a tumor, and furthermore, it is possible to make the droplet have a tissue selectivity by adding the molecular probe. Ultrasound imaging higher in tissue selectivity is enabled by using such a phase-shift type ultrasound contrast agent.

Meanwhile, it is disclosed that in order to stably causing a phase shift of such a phase shift ultrasound contrast agent is requested a temporally averaged acoustic intensity surpassing 0.72 W/cm$^2$ of an upper limit usable in a usual ultrasonic apparatus for a diagnosis and therapy (for example, see Ultrasound Contrast Image 92 (Proc. 4$^{th}$ Intern Symp.) by Kawabata et al. (2004)).

In addition, as a new diagnostic modality for using an ultrasound is disclosed radiation pressure imaging (for example, see pages 1087-1093 in Trans. IEEE Medical Imag. 23 by Alizards et al. (2004)). In the Medical Imag. 23 is proposed the diagnostic modality for performing a diagnosis, using an ultrasound not less than an acoustic intensity restricted in a conventional ultrasonic apparatus for a diagnosis and therapy.

By combining the phase-shift type ultrasound contrast agent and an ultrasound therapy, it is enabled to restrict a micro bubble to a target position and to reduce an ultrasound exposure amount in the ultrasound therapy.

As described above, because a micro bubble is produced in making an image, using the phase-shift type ultrasound contrast agent, it is enabled to apply the contrast agent to a therapy as well as a diagnosis.

However, because a conventional ultrasonic apparatus for a diagnosis and therapy cannot start a therapy in conjunction with the production of a micro bubble from the phase-shift type ultrasound contrast agent, there is a problem that an ultrasound of a comparatively high intensity is requested to be exposed in producing the micro bubble from the contrast agent.

Consequently, an ultrasonic apparatus for a diagnosis and therapy is strongly requested that can perform the therapy in conjunction with making imaging by a phase-shift type ultrasound contrast agent.

SUMMARY OF THE INVENTION

In order to solve the problem, an apparatus of the present invention is an ultrasonic apparatus for a diagnosis and therapy comprising: a first ultrasound probe for exposing an ultrasound for a phase shift; a second ultrasound probe for exposing an ultrasound for a diagnosis; an ultrasound exposure apparatus for exposing an ultrasound for a therapy; an echo detection device for detecting an ultrasound echo; a control part for the phase shift for causing the phase shift in an ultrasound contrast agent by exposing the ultrasound for the phase shift through the first ultrasound probe; a control part for the diagnosis for detecting the phase shift of the contrast agent, using the ultrasound echo detected by the echo detection device with corresponding to an exposure of the ultrasound for the diagnosis by the second ultrasound probe; a difference calculation device for calculating a difference over time of the phase shift detected by the control part for the diagnosis; a device for positioning for deciding a target position where the difference is produced; and a control part for the therapy for exposing the ultrasound for the therapy to the decided target position through the ultrasound exposure apparatus.

Thus configured, it is enabled to move an exposure of an ultrasound for a phase shift and that of an ultrasound for a diagnosis in conjunction with each other, and to reduce the exposure amount of the ultrasound.

BRIEF DESCRIPTION OF THE DRAWINGS

FIG. 3 is a flowchart explaining one example of a method of diagnosing and treating an inspected body, using an ultrasonic apparatus for a diagnosis and therapy of the embodiment.

FIGS. 4A to 4D are drawings respectively verifying phase shift differences of a contrast agent in cases that waveforms of ultrasonic pulses for a phase shift are changed.

FIG. 5 is a drawing in an example 2 showing one example of diagnostic images displayed in a display device.

BEST MODE FOR CARRYING OUT THE INVENTION

Here will be described a best mode for carrying out the present invention (hereinafter referred to as "embodiment") in detail, referring to drawings as needed.

Figure 1:
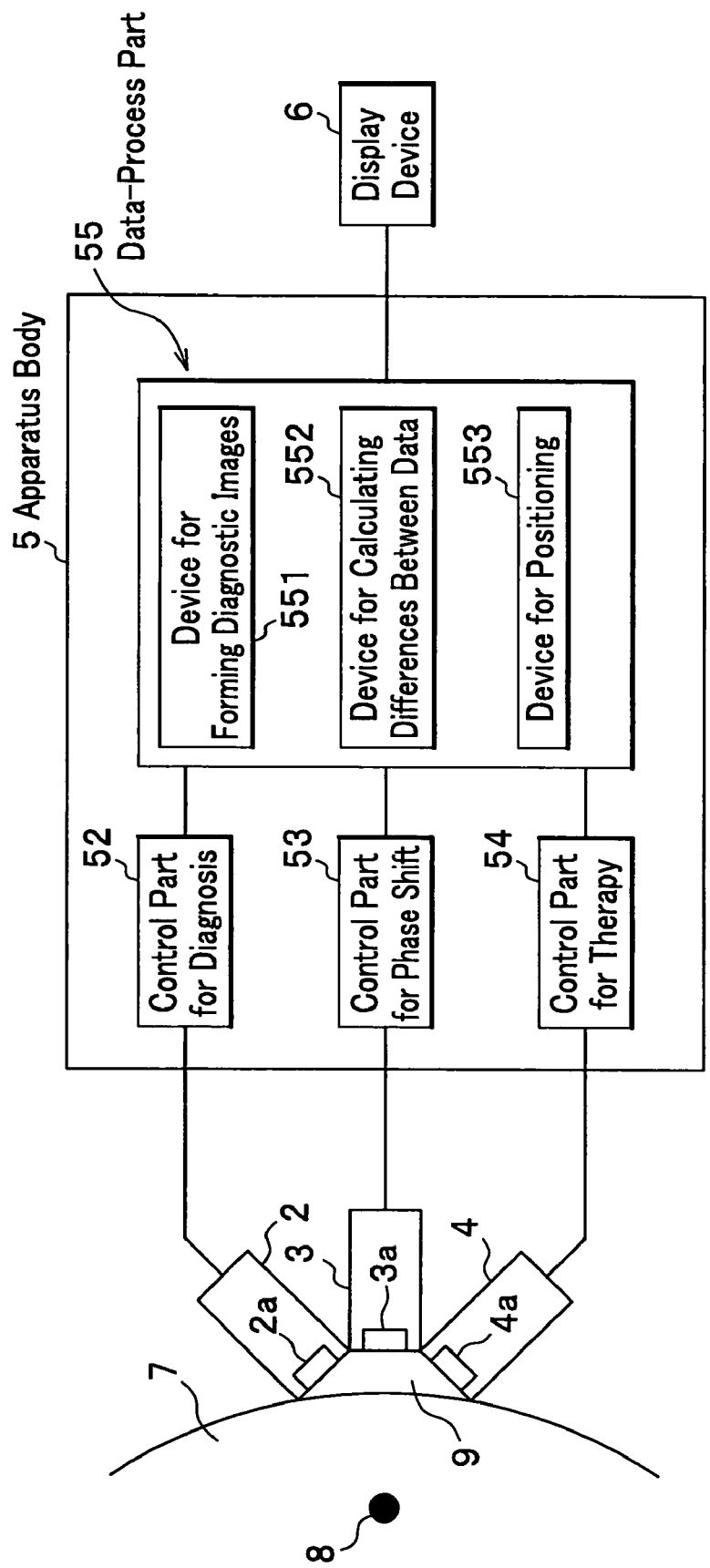
FIG. 1 is a block diagram showing a configuration of an ultrasonic apparatus for a diagnosis and therapy of an embodiment of the present invention.

As shown in FIG. 1, an ultrasonic apparatus 1 for a diagnosis and therapy comprises a diagnostic probe 2, a phase shift probe 3, a therapeutic probe 4, and an apparatus body 5, and a display device 6.

In addition, it is assumed that a predetermined phase-shift type ultrasound contrast agent (hereinafter referred to as "contrast agent") has been dosed in an inspected body 7 containing a target position 8. The contrast agent is not specifically limited in its composition if a phase shift thereof occurs from a liquid to a gas at least in its part by exposing an ultrasound for a phase shift.

Meanwhile, if although an "inspected body" means an object for a diagnosis and therapy by the ultrasonic apparatus 1 of the embodiment, it has a constitution inside which a phase shift can occur, anything is available. For example, the inspected body 7 is such a living body tissue of any one of an animal (including a human) and a plant, and a solution held in a container.

<Diagnostic Probe>

The diagnostic probe 2 exposes an ultrasonic pulse for a diagnosis to the target position 8 of the inspected body 7, and receives an ultrasound echo corresponding to the ultrasonic pulse for the diagnosis.

The diagnostic probe 2 comprises a vibrator 2a for converting an electric signal to a vibration and vice versa. As the vibrator 2a can be utilized, for example, such a magnetic strain resonator and a piezoelectric resonator. In addition, in order to diagnose a predetermined range in the inspected body 7, it is preferable to be able to display a plurality of scan lines corresponding to each vibrator 2a by arraying a plurality of vibrators 2a. Meanwhile, it is preferable for the vibrators 2a to be arrayed in any one of a flat plane and a convex plane.

In addition, the diagnostic probe 2 is connected to the apparatus body 5.

<Phase Shift Probe>

The phase shift probe 3 exposes an ultrasonic pulse for a phase shift to the target position 8 of the inspected body 7 in order to cause a phase shift in a contrast agent dosed in the inspected body 7.

It is enabled to make a configuration of the phase shift probe 3 similar to that of the diagnostic probe 2. Meanwhile, it is preferable for a vibrator 3a to be arrayed in any one of a flat plane and a convex plane (in a case that the vibrator is one, to be formed in any one of a flat plane and a convex plane) in order to converge an ultrasound.

In addition, the phase shift probe 3 is connected to the apparatus body 5.

<Therapeutic Probe>

The therapeutic probe 4 exposes an ultrasound for a therapy for the target position 8 of the inspected body 7 in order to treat the inspected body 7.

It is also enabled to make a configuration of the therapeutic probe 4 similar to that of the diagnostic probe 2. Meanwhile, it is preferable for a vibrator 4a to be arrayed in any one of a flat plane and a convex plane (in a case that the vibrator is one, to be formed in any one of a flat plane and a convex plane) in order to converge an ultrasound.

In addition, the therapeutic probe 4 is connected to the apparatus body 5.

In addition, each of the probes 2 to 4 is usually installed at the inspected body 7 through an acoustic coupling 9 in order to sensitively send and receive an ultrasonic pulse.

<Apparatus Body>

The apparatus body 5 performs processing for an electric signal corresponding to an ultrasound echo collected from the inspected body 7, controls sending and receiving an ultrasound, controls an ultrasound image display, and the like.

As shown in FIG. 1, the apparatus body 5 comprises a control part 52 for a diagnosis, a control part 53 for a phase shift, a control part 54 for a therapy, and a data-process part 55.

Meanwhile, each of the parts 52 to 55 comprises a memory consisting of such a CPU (Central Processing Unit), a ROM (Read Only Memory), and a RAM (Random Access Memory); a hard disk; and the like. Each of the parts 52 to 55 within the apparatus body 5 corresponds to a program or data stored in the memory or the hard disk. Then it is assumed that the CPU reads the program into the memory, performs calculation processing, and thereby, each processing is realized.

In addition, each of the parts 52 to 54 further comprises such an amplifier circuit and an A/D converter circuit not shown.

The control part 52 for the diagnosis is electrically connected to the diagnostic probe 2 and controls sending and receiving an ultrasound for a diagnosis.

In addition, the control part 52 for the diagnosis is configured to be able to send and receive an ultrasound of a frequency of roughly an extent of 2 to 10 MHz and a temporally averaged acoustic intensity not more than 0.72 W/cm$^2$ usable in a usual ultrasound diagnostic apparatus.

Here will be described a procedure of controlling sending and receiving the ultrasound for the diagnosis.

Firstly, the control part 52 for the diagnosis produces an electric signal (appropriately called "pulse signal") and sends it to the diagnostic probe 2.

Specifically in a case of a pulse inversion mode, the control part 52 produces the pulse signal so as to expose a predetermined basic wave and a reverse phase basic wave to one scan line, and sends them to the diagnostic probe 2.

Then, the control part 52 receives an echo signal from the diagnostic probe 2.

Specifically in a case of the pulse inversion mode, a basic wave is cancelled by a reverse phase basic wave out of the basic wave and a higher harmonic wave contained in an ultrasound echo, and thereby, mainly the higher harmonic wave results in being received by the diagnostic probe 2. The higher harmonic wave tends to occur if a larger component of a volume change is contained in the inspected body 7. Accordingly, the pulse inversion mode is suitable for detecting a gas inside the inspected body 7, compared to a B mode generally used in an ultrasound diagnosis. Meanwhile, the control part 52 of the embodiment is not limited to the pulse inversion mode if it can detect a phase shift.

In addition, in the control part 52 of the embodiment there is a fear that an accuracy of a diagnostic image is degraded by receiving not only an echo signal corresponding to the ultrasonic pulse for the diagnosis but also echo signals corresponding to ultrasonic pulses for a phase shift and a therapy. Consequently, it may be configured that, for example, a filter for restricting a frequency and a voltage out of a predetermined bandwidth is provided in the control part 52.

Then the control part 52 amplifies the received echo signal by the amplifier circuit not shown, samples it by a sampling frequency suitable for signal processing by the A/D converter circuit, and converts it to a digital signal.

Then the digital signal corresponding to the echo signal is output to the data-process part 55. 35

The control part 53 for the phase shift is electrically connected to the phase shift probe 3, and controls sending an ultrasound for a phase shift. The control part 53 is configured to be able to expose an ultrasound in a range of 0.5 to 10 W/cm$^2$ in temporally averaged acoustic intensity, wherein the ultrasound is any one of a single frequency selected from a range of 0.5 to 10 MHz and a frequency where on a basic frequency selected from a range of 0.5 to 5 MHz is superposed a double frequency of the basic frequency.

The control part 53 produces an electric signal corresponding to the ultrasonic pulse for the phase shift, and sends it to the phase shift probe 3.

If the ultrasonic pulse for the phase shift is exposed to a contrast agent dosed in the inspected body 7, in the contrast agent the phase shift occurs from a liquid to a gas. Such the phase shift of the contrast agent can be detected more clearly in a case that the control part 52 for the diagnosis is the pulse inversion mode.

Meanwhile, it is preferable that the ultrasonic pulse for the phase shift is weak as much as possible in acoustic intensity in a range of being able to cause the phase shift in the contrast agent in order to prevent an excessive ultrasound exposure to the inspected body 7.

In addition, although a larger energy is requested to produce a cavitation caused by phase shift, the inventors et al. have proved that such the energy as in producing the cavitation is not needed to maintain the cavitation once caused. If it is enabled to lessen an energy for maintaining the cavitation, it is enabled to reduce an ultrasound exposure amount to the inspected body 7, and to alleviate a burden of the inspected body 7.

Figure 2A:
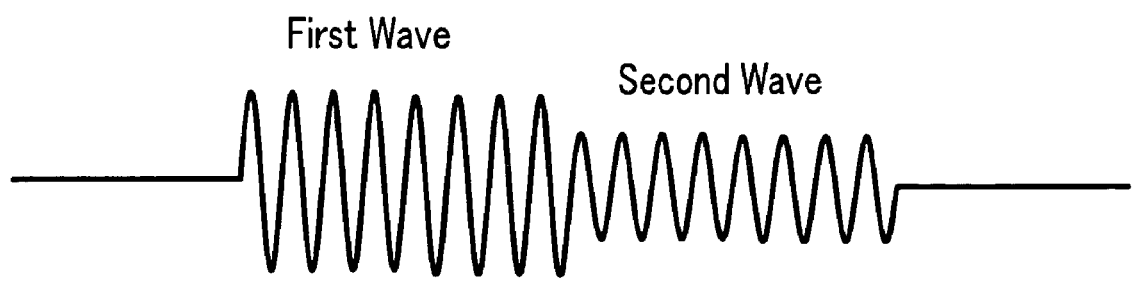
FIGS. 2A and 2B are drawings respectively showing waveforms of ultrasonic pulses for a phase shift of the embodiment.
Figure 2B:
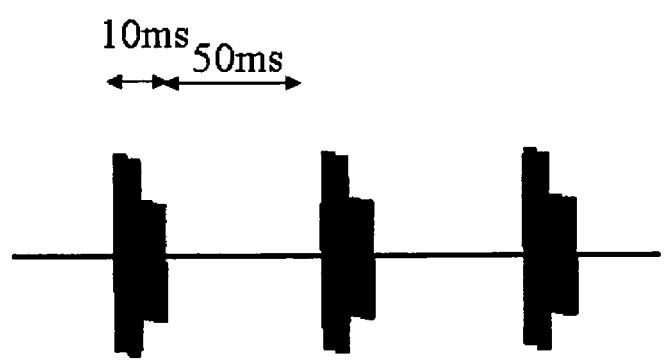

FIGS. 2A and 2B are drawings respectively showing waveforms of ultrasonic pulses for a phase shift of the embodiment; FIG. 2A is a drawing explaining waveforms of ultrasonic pulses; and FIG. 2B is a schematic drawing explaining continuous ultrasonic pulses. In FIGS. 2A and 2B a horizontal axis is a time; a vertical axis is an acoustic intensity of an ultrasonic pulse. As shown in FIG. 2A, the ultrasonic pulses for the phase shift are configured with a first wave and a second wave. The first wave causes a phase shift of a contrast agent; the second wave maintains the caused phase shift of the contrast agent. In addition, as shown in FIG. 2B, it is preferable to provide an interval of 50 ms for an ultrasound of 10 ms in order to more effectively cause the phase shift of the contrast agent.

Here, although an acoustic intensity requested is preferably not less than 0.72 W/cm² in order to stably cause a phase shift as shown in Ultrasound Contrast Image 92 (Proc. 4$^{th}$ Intern Symp.) by Kawabata et al. (2004) described before, the phase shift can be caused if the acoustic intensity is at least 0.1 W/cm².

In addition, an acoustic intensity requested for maintaining the phase shift is preferably in a range of one fourth to one fold of the first wave. The acoustic intensity of the second wave is prescribed in an example 1 described later.

In addition, returning to FIG. 1, the control part 53 for the phase shift comprises an ultrasonic pulse scan device not shown for scanning the ultrasonic pulse for the phase shift (specifically its focus). The ultrasonic pulse scan device may also be any configuration of, for example, mechanically moving the phase shift probe 3 and of controlling only a direction of an ultrasound beam exposed by controlling a pulse signal.

The control part 54 for the therapy is electrically connected to the therapeutic probe 4 and controls sending an ultrasound pulse for a therapy.

The control part 54 produces an electric signal corresponding to the ultrasonic pulse for the therapy and sends it to the therapeutic probe 4. The control part 54 is configured to be able to expose any one of an ultrasound selected from a range of 0.5 to 10 MHz and a frequency where on a basic frequency selected from a range of 0.5 to 5 MHz is superposed a double frequency of the basic frequency; and an acoustic intensity can be made an arbitrary value selected from a range of 1 to 1000 W/cm².

As described before, the therapeutic methods by ultrasound are mainly classified into the thermal coagulation therapy and the therapy by cavitation action. In accordance with the control part 54 of the embodiment, in any case can be supplied an electric signal for exposing an ultrasonic pulse of a proper acoustic intensity.

Generally, although the stronger the acoustic intensity, the more effective the ultrasound of the thermal coagulation therapy is, the embodiment obtains a sufficient effect because of utilizing a micro bubble even if, for example, the acoustic intensity of the ultrasound is not more than 1000 W/Cm².

In addition, although a cavitation can be produced enough by an ultrasound consisting of one frequency, it is well known that an ultrasound where two frequencies are superposed can more efficiently produce the cavitation as indicated by a pamphlet of WO 94/06380. Because the embodiment is the configuration of being able to exposing an ultrasound where two frequencies are superposed, it obtains a sufficient therapeutic effect even in an ultrasound of a lower acoustic intensity.

In addition, the control part 54 for the therapy comprises an ultrasonic pulse movement device not shown for moving the ultrasonic pulse for the therapy (specifically its focus). The ultrasonic pulse movement device may be any configuration of, for example, mechanically moving the therapeutic probe 4, and of controlling only a direction of an ultrasound beam exposed by controlling a pulse signal.

The data-process part 55 processes digital data based on an echo signal acquired by the control part 52 for the diagnosis, and supplies control information to the control part 53 for the phase shift and the control part 54 for the therapy.

The data-process part 55 comprises, for example, a device 551 for forming diagnostic images, a device 552 for calculating differences between data, and a device 553 for positioning.

The device 551 for forming diagnostic images processes to produce a diagnostic image such as a pulse inversion mode tomogram from a digital signal based on an echo signal. The production processing of the diagnostic image by the device 551 can be performed in a field of an ultrasound image diagnosis by a conventional well known method.

Then the diagnostic image produced by the device 551 is output to the device 552 for calculating differences between data.

The device 552 digitalizes brightness in diagnostic images before an ultrasonic pulse for a phase shift and after an exposure, respectively, and calculates their difference.

Then the difference calculated by the device 552 is output to the device 553 for positioning.

The device 553 decides a target position where a phase shift is produced by comparing the difference calculated by the device 552 with a predetermined threshold. To be more precise, in a case that the difference exceeds the predetermined threshold, the device 553 decides the target position, assuming that the phase shift is produced; in a case that the difference does not exceed the predetermined threshold, the device 553 assumes that the phase shift is not produced.

Then information of the target position decided by the device 553 is output to the display device 6 and the control parts 53 and 54.

<Ultrasonic Method for Diagnosis and Therapy>

Next will be described one example of a method for diagnosing and treating the inspected body 7 by using the ultrasonic apparatus 1, referring to FIG. 3.

Firstly, the control part 52 of the ultrasonic apparatus 1 acquires an electric signal of an ultrasound echo corresponding to an ultrasonic pulse for a diagnosis with respect to the target position 8 (diagnosis region) of the inspected body 7, and converts it to a digital signal (step S01).

Next, the data-process part 55 of the ultrasonic apparatus 1 makes a diagnostic image (before a phase shift) of the target position 8 by the device 551, based on the digital signal, and notifies (step S02) the control part 53 of having made the diagnostic image (before the phase shift).

Then if the control part 53 of the ultrasonic apparatus 1 receives the notification of having made the diagnostic image (before the phase shift), it starts to scan (step S03) the ultrasonic pulse for the phase shift in the target position 8.

Meanwhile, scanning the ultrasonic pulse for the phase shift is performed, including a region where the diagnostic image is formed.

Then the data-process part 55 of the ultrasonic apparatus 1 makes (step S04) a diagnostic image (after the phase shift) for every scan (every movement of a focus) of the ultrasonic pulse for the phase shift by the device 551.

Then the data-process part 55 of the ultrasonic apparatus 1 calculates (step S05) a difference of brightness by the device 552, comparing the diagnostic images before and after the phase shift for every scan.

Then the data-process part 55 of the ultrasonic apparatus 1 compares (step S06) the difference of the brightness with a threshold by the device 553.

In a case that the difference of the brightness does not exceed the threshold (No in the step S06), the control part 53 of the ultrasonic apparatus 1 moves (step S10) the focus of the ultrasonic pulse for the therapy to a target position where the pulse is not yet exposed.

In a case that the difference of the brightness exceeds the threshold (Yes in the step S06), the control part 53 of the ultrasonic apparatus 1 lowers (step S07) the acoustic intensity of the ultrasonic pulse for the phase shift to one fourth to one fold thereof.

Then the data-process part 55 of the ultrasonic apparatus 1 decides (step S08) a target position (which matches the focus of the ultrasonic pulse for the phase shift during exposure in many cases) by the device 553 where the difference of the brightness has exceeded the threshold.

Then the control part 54 of the ultrasonic apparatus 1 exposes (step S09) the ultrasonic pulse for the therapy to the decided target position.

Then the control part 53 of the ultrasonic apparatus 1 moves (step S10) the focus of the ultrasonic pulse for the therapy to a target position where the pulse is not yet exposed.

Thus the following effects can be obtained in the embodiment:

Because it is configured that exposing an ultrasonic pulse for a phase shift and that for a diagnosis are made to move in conjunction with each other, it is enabled to reduce an exposure amount of the ultrasounds.

In addition, by configuring the ultrasonic pulse for the phase shift with the first wave and the second wave lower in acoustic intensity than the first wave, it is enabled to confirm the target position 8 while suppressing an excess exposure of the ultrasounds to the inspected body 7 and to perform a therapy.

Meanwhile, the present invention is not limited to the embodiment, and various variations are available without departing from the spirit and scope of the invention.

For example, in the embodiment, although the exposure position of the ultrasonic pulse for the therapy is decided by calculating the difference of brightness of the diagnostic images before and after exposing the ultrasonic pulse for the phase shift, a method for deciding the exposure position of the ultrasonic pulse for the therapy is not limited thereto described above. For example, the exposure position may be decided by calculating a difference between levels of the echo signals. Or else the exposure position may be decided by calculating a difference of the digital signals corresponding to the echo signals. In addition, it is preferable to compare each even harmonic wave component of central frequencies of ultrasonic pulses for the diagnosis before and after the exposures of ultrasonic pulses for the phase shift.

Meanwhile, In any case it is enabled to image a target position where a difference of the signals is produced and to display it in the display device 6.

In addition, the diagnostic probe 2, the phase shift probe 3, and the therapeutic probe 4 can also be combined without being made independent configurations, respectively. In this case it is enabled to achieve to image the target position by controlling each sending timing of pulse signals sent from the control parts 52 to 54 corresponding to the probes 2 to 4.

EXAMPLE 1

In an example 1 is verified a phase-shift type ultrasound contrast agent in a case that a waveform of an ultrasonic pulse for a phase shift is changed. In the example 1, as the contrast agent was used an emulsion type agent disclosed in Ultrasound Contrast Image 92 (Proc. 4$^{th}$ Intern Symp.) by Kawabata et al. (2004) described before.

FIGS. 4A to 4D are drawings respectively verifying phase shift differences of a contrast agent in cases that waveforms of ultrasonic pulses for a phase shift are changed. Although in FIGS. 4A to 4D an acoustic intensity of a first wave is 4 W/cm$^2$ (temporal averaged) in common, a second wave is changed to a predetermined acoustic intensity. Meanwhile, an ultrasound frequency is 3.4 MHz in both of the first and second waves.

As shown in FIGS. 4A to 4C, in cases that the second wave is not less than 1 W/cm$^2$ with respect to 4 W/cm$^2$ of the first wave, it was enabled to detect the phase shift even if the acoustic intensity of the second wave is made lower than that of the first wave. On the other hand, as shown in FIG. 4D, in a case that the second wave is 0.5 W/cm$^2$ with respect to 4 W/cm$^2$ of the first wave, it was not enabled to detect the phase shift.

In other words, in accordance with the example 1 was indicated that a phase shift state of the contrast agent is maintained in a range of the acoustic intensity of the second wave being one fourth to one fold of that of the first wave.

EXAMPLE 2

In an example 2 was practically performed a diagnosis and therapy, using the ultrasonic apparatus 1 of the embodiment. An object for the diagnosis and therapy is colon 26 tumor subdermally implanted in a mouse.

As a contrast agent was used the emulsion type agent disclosed in Ultrasound Contrast Image 92 (Proc. 4$^{th}$ Intern Symp.) by Kawabata et al. (2004) described above.

In addition, for the diagnosis was used an ultrasonic pulse of 7.5 MHz; for the phase shift, an ultrasonic pulse of 3.4 MHz and 4 W/cm$^2$ (temporal averaged) (10 ms ON, 50 ms OFF); and for the therapy, an ultrasonic pulse of 3.4 MHz and 50 W/cm$^2$ (temporal averaged) (10 ms ON, 50 ms OFF). Meanwhile, in the example 2 was not scanned the ultrasound for the phase shift.

FIG. 5 is a drawing in the example 2 showing one example of diagnostic images displayed in a display device; (B1) and (B4) are diagnostic images of a B mode used in a general ultrasound diagnosis; and (P1), (P2), (P3), and (P4) are diagnostic images of the pulse inversion mode of the embodiment.

In addition, in FIG. 5 each region indicated by an outline square on a black background is a target position where the phase shift of the contrast agent is observed by exposing the ultrasonic pulse for the phase shift.

The (B1) and (P1) at respective first stages are diagnostic images after 15 minutes of a dose of the contrast agent and before exposing the ultrasonic pulse for the phase shift.

The (P2) at the second stage is a diagnostic image during exposing the ultrasonic pulse for the phase shift. Brightness of an exposure position surrounded by the outline square on the black background of the (P2) results in being higher than that of the (P1).

The (P3) at the third stage is a diagnostic image during exposing the ultrasonic pulse for the therapy. Meanwhile, as soon as the ultrasonic pulse for the phase shift is stopped after three seconds from its start, the ultrasonic pulse for the therapy is started to expose the same position.

Brightness of an exposure position of the (P3) results in being more remarkable than that of the (P2). This is because even if a micro bubble is collapsed by the ultrasonic pulse for the therapy, a signal in its collapse is detected in the diagnostic image.

The (B4) and the (P4) at respective fourth stages are diagnostic images when the ultrasonic pulse for the therapy is stopped after exposing the ultrasonic pulse for the diagnosis for 60 seconds.

Comparing the (B4) with the (B1), an obvious tissue change is observable on the diagnostic images by exposing the ultrasonic pulse for the therapy.

Figure 6:
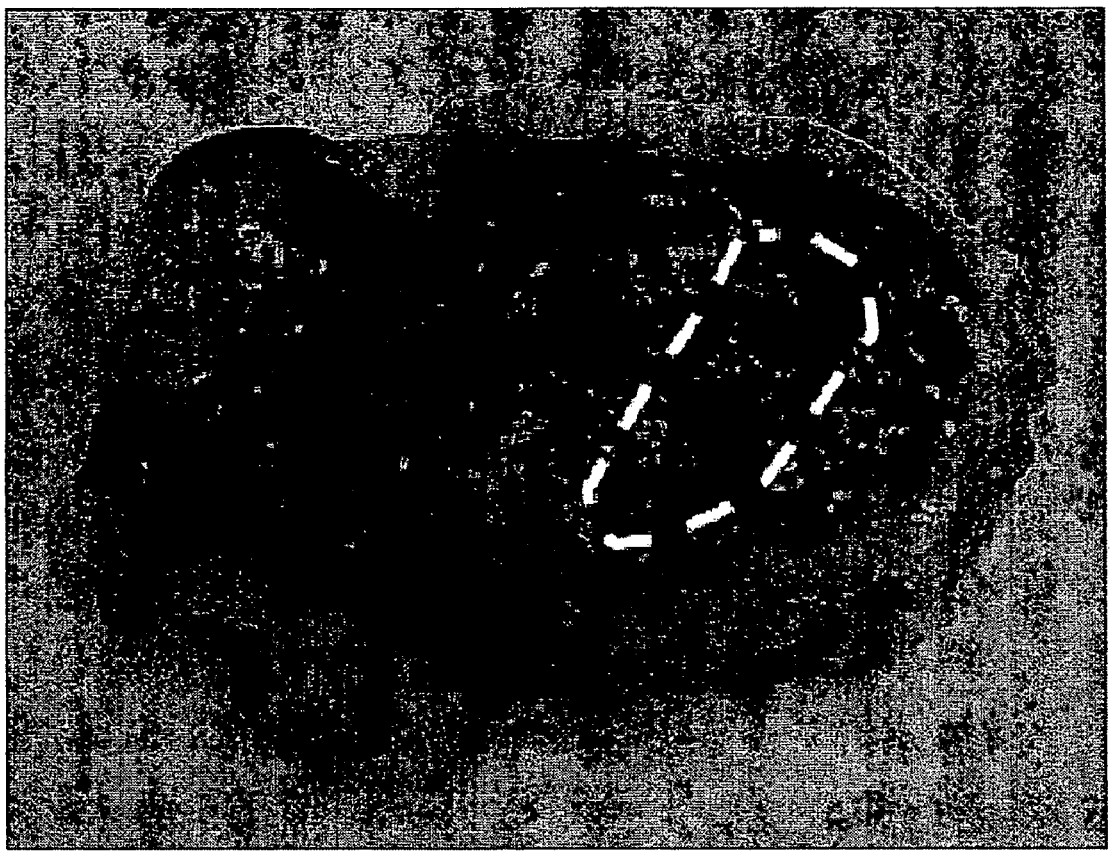
FIG. 6 is a drawing showing a tumor segment after exposing an ultrasound for a therapy to it.

FIG. 6 is a drawing showing a tumor segment after exposing an ultrasonic pulse for a therapy. At a brightness change position of the (P4) of FIG. 5 is observed a tumor necrosis.

Meanwhile, although not shown, as a result of having performed a study similar to the example 2 by frequencies of 0.5 and 1.0 MHz (each acoustic intensity, 10 W/cm$^2$), a tumor necrosis effect equivalent to that of the example 2 was obtained.

What is claimed is:

1. An ultrasonic apparatus for a diagnosis and therapy comprising:
 a first ultrasound probe configured to generate an ultrasound wave for a phase shift;
 a second ultrasound probe configured to generate an ultrasound wave for a diagnosis;
 a third ultrasound probe configured to generate an ultrasound wave for a therapy;
 an echo detection device configured to detect an ultrasound echo;
 a first control part configured to cause the phase shift in a nano droplet ultrasound contrast agent by exposing said ultrasound for the phase shift through said first ultrasound probe;
 a second control part configured to detect the phase shift of said ultrasound contrast agent using a nano droplet ultrasound echo detected by said echo detection device based on an exposure of said ultrasound for diagnosis by said second ultrasound probe;
 a difference calculation device configured to calculate a difference over time of said phase shift detected by said second control part for the diagnosis;
 a positioning device configured to decide a target position where said difference is produced; and
 a third control part configured to expose said ultrasound for the therapy to said decided target position through said third ultrasound probe;
 wherein said first ultrasound probe is further configured to generate the ultrasound wave including a first wave and a second wave, and
 wherein the first ultrasound probe is further configured to generate the second wave after the first wave and having an acoustic density which is not more than that of said first wave.

2. The ultrasonic apparatus according to claim 1, wherein said second wave is not less than one fourth fold and not more than one fold of said first wave in acoustic intensity.

3. The ultrasonic apparatus according to claim 1, wherein a frequency of said ultrasound for the phase shift controlled by said first control part for said phase shift is not less than 0.5 MHz and not more than 10 MHz.

4. The ultrasonic apparatus according to claim 1, wherein a frequency of said ultrasound for the diagnosis controlled by said second control part for said diagnosis is not less than 0.5 MHz and not more than 10 MHz.

5. The ultrasonic apparatus according to claim 4, wherein an acoustic intensity of said ultrasound for the therapy controlled by said third control part for said therapy is not less than 1 W/cm$^2$ and not more than 1000 W/cm$^2$.

* * * * *